US009610276B2

(12) United States Patent
Guthrie

(10) Patent No.: US 9,610,276 B2
(45) Date of Patent: *Apr. 4, 2017

(54) COMPOSITIONS AND METHODS FOR GLYCEMIC CONTROL OF SUBJECTS WITH IMPAIRED FASTING GLUCOSE

(71) Applicant: KGK SYNERGIZE, INC., London (CA)

(72) Inventor: Najla Guthrie, London (CA)

(73) Assignee: KGK Synergize, Inc., London (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/812,256

(22) Filed: Jul. 29, 2015

(65) Prior Publication Data
US 2015/0328184 A1 Nov. 19, 2015

Related U.S. Application Data

(63) Continuation of application No. 13/919,589, filed on Jun. 17, 2013, now Pat. No. 9,132,117.

(51) Int. Cl.
| | |
|---|---|
| *A61K 31/355* | (2006.01) |
| *A61K 31/352* | (2006.01) |
| *A61K 31/353* | (2006.01) |
| *A61K 38/16* | (2006.01) |
| *A61K 45/06* | (2006.01) |
| *A61K 31/155* | (2006.01) |
| *A61K 31/366* | (2006.01) |

(52) U.S. Cl.
CPC .......... *A61K 31/352* (2013.01); *A61K 31/155* (2013.01); *A61K 31/353* (2013.01); *A61K 31/355* (2013.01); *A61K 31/366* (2013.01); *A61K 38/168* (2013.01); *A61K 45/06* (2013.01)

(58) Field of Classification Search
USPC ........................................ 514/458, 456, 473
See application file for complete search history.

(56) References Cited

U.S. PATENT DOCUMENTS

| | | |
|---|---|---|
| 3,674,836 A | 7/1972 | Creger |
| 3,692,895 A | 9/1972 | Nelson et al. |
| 3,803,237 A | 4/1974 | Lednicer et al. |
| 3,852,502 A | 12/1974 | Bishov et al. |
| 3,867,541 A | 2/1975 | Robbins |
| 3,903,266 A | 9/1975 | Robbins |
| 3,993,793 A | 11/1976 | Finney |
| 4,368,213 A | 1/1983 | Hollenbach et al. |
| 4,395,417 A | 7/1983 | Hall et al. |
| 4,499,303 A | 2/1985 | Wyrick et al. |
| 4,591,600 A | 5/1986 | Creuzet et al. |
| 4,603,142 A | 7/1986 | Burger et al. |
| 4,684,520 A | 8/1987 | Bertelli |
| 4,780,456 A | 10/1988 | Pistolesi |
| 4,814,172 A | 3/1989 | Chavkin et al. |
| 4,937,086 A | 6/1990 | Prosise |
| 5,041,425 A | 8/1991 | Hasegawa et al. |
| 5,043,323 A | 8/1991 | Bombardelli et al. |
| 5,217,992 A | 6/1993 | Wright et al. |
| 5,320,861 A | 6/1994 | Mantius et al. |
| 5,336,685 A | 8/1994 | Prochaska et al. |
| 5,348,974 A | 9/1994 | Wright et al. |
| 5,545,398 A | 8/1996 | Perricone |
| 5,580,545 A | 12/1996 | Washino et al. |
| 5,591,772 A | 1/1997 | Lane et al. |
| 5,616,355 A | 4/1997 | Haast et al. |
| 5,808,137 A | 9/1998 | Bombardelli et al. |
| 5,855,892 A | 1/1999 | Potter et al. |
| 5,912,265 A | 6/1999 | Bombardelli et al. |
| 5,919,818 A | 7/1999 | Lane et al. |
| 5,932,562 A | 8/1999 | Ostlund, Jr. |
| 5,952,373 A | 9/1999 | Lanzendorfer et al. |
| 5,952,393 A | 9/1999 | Sorkin, Jr. |
| 5,955,269 A | 9/1999 | Ghai et al. |
| 6,063,776 A | 5/2000 | Ostlund, Jr. |
| 6,086,915 A | 7/2000 | Zeligs et al. |
| 6,087,385 A | 7/2000 | Pershadsingh et al. |
| 6,096,364 A | 8/2000 | Bok et al. |
| 6,133,312 A | 10/2000 | Elson |
| 6,136,349 A | 10/2000 | Karppanen et al. |
| 6,143,770 A | 11/2000 | Lane et al. |
| 6,184,246 B1 | 2/2001 | Manthey et al. |
| 6,239,114 B1 | 5/2001 | Guthrie et al. |
| 6,239,144 B1 | 5/2001 | Guthrie |
| 6,251,400 B1 | 6/2001 | Guthrie |
| 6,312,703 B1 | 11/2001 | Orthoefer |
| 6,528,042 B1 | 3/2003 | Brown et al. |
| 6,579,544 B1 | 6/2003 | Rosenberg et al. |

(Continued)

FOREIGN PATENT DOCUMENTS

| | | |
|---|---|---|
| CA | 2342608 A1 | 3/2000 |
| CA | 2346325 A1 | 4/2000 |

(Continued)

OTHER PUBLICATIONS

U.S. Appl. No. 60/560,284, filed Apr. 8, 2004, Guthrie.
U.S. Appl. No. 60/574,487, filed May 26, 2004, Guthrie.
U.S. Appl. No. 60/574,490, filed May 26, 2004, Guthrie.
U.S. Appl. No. 60/574,655, filed May 26, 2004, Guthrie.
U.S. Appl. No. 60/694,720, filed Jun. 28, 2005, Guthrie et al.
U.S. Appl. No. 67/735,660, filed Nov. 10, 2005, Guthrie.
U.S. Appl. No. 60/771,752, filed Feb. 9, 2006, Guthrie.
U.S. Appl. No. 60/801,682, filed May 19, 2006, Guthrie.
U.S. Appl. No. 12/250,334, filed Oct. 13, 2008, Guthrie.
U.S. Appl. No. 12/250,332, filed Oct. 13, 2008, Guthrie.
U.S. Appl. No. 12/301,573, filed May 21, 2007, Guthrie et al.
U.S. Appl. No. 12/431,450, filed Apr. 28, 2009, Guthrie et al.

(Continued)

*Primary Examiner* — Rei-Tsang Shiao
(74) *Attorney, Agent, or Firm* — Porzio, Bromberg & Newman P.C.

(57) ABSTRACT

Compositions and methods for providing anti-diabetic and anti-hyperlipidemia benefits to diabetic subjects currently on medication but not meeting recommended targets for blood glucose, HbA1c, blood pressure and total cholesterol.

19 Claims, 2 Drawing Sheets

(56) References Cited

U.S. PATENT DOCUMENTS

| | | |
|---|---|---|
| 6,773,719 B2 | 8/2004 | Rodrigueza et al. |
| 6,858,618 B2 | 2/2005 | Raza et al. |
| 6,864,280 B2 | 3/2005 | Igarashi et al. |
| 6,987,125 B1 | 1/2006 | Guthrie |
| 7,683,095 B2 | 3/2010 | Guthrie |
| 9,132,117 B2 * | 9/2015 | Guthrie ............... A61K 31/353 |
| 2001/0055627 A1 | 12/2001 | Guthrie et al. |
| 2002/0054924 A1 | 5/2002 | Leahy et al. |
| 2002/0090404 A1 | 7/2002 | Guthrie et al. |
| 2002/0090405 A1 | 7/2002 | Guthrie et al. |
| 2002/0127259 A1 | 9/2002 | Orthoefer |
| 2003/0144219 A1 | 7/2003 | Phinney et al. |
| 2004/0152641 A1 | 8/2004 | Guthrie et al. |
| 2004/0176311 A1 | 9/2004 | Mo et al. |
| 2005/0227930 A1 | 10/2005 | Guthrie |
| 2006/0013802 A1 | 1/2006 | Shafer |
| 2006/0013861 A1 | 1/2006 | Guthrie |
| 2006/0013901 A1 | 1/2006 | Guthrie |
| 2006/0013902 A1 | 1/2006 | Guthrie |
| 2006/0028088 A1 | 2/2006 | McFarland et al. |
| 2007/0111953 A1 | 5/2007 | Gutrie et al. |
| 2007/0117763 A1 * | 5/2007 | Guthrie ............... A61K 31/352 514/27 |
| 2007/0184132 A1 | 8/2007 | Guthrie |
| 2009/0156663 A1 | 6/2009 | Guthrie |
| 2009/0156665 A1 | 6/2009 | Guthrie |
| 2009/0163581 A1 | 6/2009 | Guthrie |
| 2010/0015255 A1 | 1/2010 | Green et al. |
| 2011/0102278 A1 | 5/2011 | Rozan |
| 2011/0135675 A1 | 6/2011 | Figdor et al. |
| 2011/0135693 A1 | 6/2011 | Barth |
| 2011/0135694 A1 | 6/2011 | Bagchi et al. |
| 2011/0250328 A1 | 10/2011 | Jaschke-Ferreri |
| 2012/0268051 A1 | 10/2012 | Wu |

FOREIGN PATENT DOCUMENTS

| | | |
|---|---|---|
| CA | 2403548 A1 | 9/2001 |
| DE | 4227806 A1 | 2/1993 |
| EP | 0229594 A2 | 7/1987 |
| EP | 0320867 A2 | 6/1989 |
| EP | 0834261 A1 | 4/1998 |
| EP | 0962150 A2 | 12/1999 |
| EP | 0968709 A1 | 1/2000 |
| EP | 11193534 | 4/2002 |
| EP | 1415549 A1 | 5/2004 |
| EP | 1829542 A1 | 9/2007 |
| EP | 2434010 A1 | 3/2012 |
| FR | 2565107 A1 | 12/1985 |
| FR | 2745981 A1 | 9/1997 |
| GB | 2222769 A | 3/1990 |
| GB | 2343101 A | 5/2000 |
| JP | 59046217 | 3/1984 |
| JP | 60199817 | 10/1985 |
| JP | H0554883 A | 1/1993 |
| JP | H06116164 A | 4/1994 |
| JP | H07135922 A | 1/1995 |
| JP | H08283154 A | 1/1996 |
| JP | H08507079 A | 7/1996 |
| JP | H08280358 A | 10/1996 |
| JP | H08310952 A | 11/1996 |
| JP | 2000295972 A | 10/2000 |
| JP | 2001200237 A | 7/2001 |
| JP | 2001200238 A | 7/2001 |
| JP | 20011240539 | 9/2001 |
| JP | 2001346537 A | 12/2001 |
| JP | 2003266031 A | 9/2003 |
| WO | WO-87/06833 A1 | 11/1987 |
| WO | WO-94/18990 A1 | 9/1994 |
| WO | WO-96/38047 A1 | 12/1996 |
| WO | WO-97/17069 A1 | 5/1997 |
| WO | WO-98/04156 A1 | 2/1998 |
| WO | WO-98/16220 A1 | 4/1998 |
| WO | WO-98/16221 A1 | 4/1998 |
| WO | WO-98/16239 A1 | 4/1998 |
| WO | WO-98/38993 A1 | 9/1998 |
| WO | WO-99/04653 A1 | 2/1999 |
| WO | WO 99/15167 | 4/1999 |
| WO | WO-99/15167 A2 | 4/1999 |
| WO | WO-99/21570 A1 | 5/1999 |
| WO | WO-99/52380 A1 | 10/1999 |
| WO | WO-99/53925 A1 | 10/1999 |
| WO | WO-99/55350 A1 | 11/1999 |
| WO | WO-99/56729 A1 | 11/1999 |
| WO | WO-00/02553 | 1/2000 |
| WO | WO-00/19998 | 4/2000 |
| WO | WO-00/62774 | 10/2000 |
| WO | WO-00/72862 A1 | 12/2000 |
| WO | WO-01/03681 | 1/2001 |
| WO | WO-01/21137 | 3/2001 |
| WO | WO-01/32031 | 5/2001 |
| WO | WO-01/32160 | 5/2001 |
| WO | WO-01/51043 | 7/2001 |
| WO | WO-01/70029 | 9/2001 |
| WO | WO 01/70029 | 9/2001 |
| WO | WO-02/22145 | 3/2002 |
| WO | WO-02/34072 | 5/2002 |
| WO | WO-02/055071 | 7/2002 |
| WO | WO 02/087567 | 11/2002 |
| WO | WO-02/087567 | 11/2002 |
| WO | WO 2005/096704 | 10/2005 |
| WO | WO-2005/096704 A2 | 10/2005 |
| WO | WO 2005/115376 | 12/2005 |
| WO | WO-2005/115376 A1 | 12/2005 |
| WO | WO 2005/115377 | 12/2005 |
| WO | WO-2005/115377 A1 | 12/2005 |
| WO | WO 2005/115378 | 12/2005 |
| WO | WO-2005/115378 A1 | 12/2005 |
| WO | WO-2006/132879 A2 | 12/2006 |
| WO | WO 2007/002897 | 1/2007 |
| WO | WO-2007/002897 A2 | 1/2007 |
| WO | WO-2007/049137 A2 | 5/2007 |
| WO | WO 2007/093853 | 8/2007 |
| WO | WO-2007/093853 A2 | 8/2007 |
| WO | WO-2007/135569 A2 | 11/2007 |
| WO | WO 2008/035208 | 3/2008 |
| WO | WO-2008/035208 A2 | 3/2008 |
| WO | WO 2007/135569 | 4/2008 |
| WO | WO 2014/203059 | 12/2014 |
| WO | WO-2014/203059 A1 | 12/2014 |

OTHER PUBLICATIONS

U.S. Appl. No. 12/580,036, filed Oct. 15, 2009, Guthrie et al.
U.S. Appl. No. 12/729,946, filed Mar. 23, 2010, Guthrie.
U.S. Appl. No. 60/287,703, filed May 2, 2001, Guthrie et al.
In the U.S. Patent and Trademark Office, Office Action in re: U.S. Appl. No. 11/704,437, dated May 12, 2008, 7 pages.
In the U.S. Patent and Trademark Office, Requirement for Restriction/Election in re: U.S. Appl. No. 11/704,437, dated Mar. 4, 2008, 5 pages.
In the U.S. Patent and Trademark Office, Notice of Allowance in re: U.S. Appl. No. 10/854,063, dated Oct. 30, 2009, 4 pages.
In the U.S. Patent and Trademark Office, Notice of Allowance in re: U.S. Appl. No. 10/854,063, dated May 26, 2009, 8 pages.
In the U.S. Patent and Trademark Office, Final Office Action in re: U.S. Appl. No. 10/854,063, dated Mar. 7, 2008, 8 pages.
In the U.S. Patent and Trademark Office, Office Action in re: U.S. Appl. No. 10/854,063, dated Apr. 2, 2007, 10 pages.
In the U.S. Patent and Trademark Office, Final Office Action in re: U.S. Appl. No. 10/854,063, dated May 25, 2006, 25 pages.
In the U.S. Patent and Trademark Office, Office Action in re: U.S. Appl. No. 10/854,063, dated Oct. 5, 2005, 5 pages.
In the U.S. Patent and Trademark Office, Office Action in re: U.S. Appl. No. 09/528,488, dated Sep. 9, 2002, 5 pages.
In the U.S. Patent and Trademark Office, Final Office Action in re: U.S. Appl. No. 09/528,488, dated May 20, 2003, 5 pages.
In the U.S. Patent and Trademark Office, Office Action in re: U.S. Appl. No. 09/528,488, dated Apr. 6, 2004, 4 pages.

(56) References Cited

OTHER PUBLICATIONS

In the U.S. Patent and Trademark Office, Notice of Allowance in re: U.S. Appl. No. 09/528,488, dated Oct. 6, 2004, 6 pages.
In the U.S. Patent and Trademark Office, Final Office Action in re: U.S. Appl. No. 11/478,970, dated Oct. 28, 2008, 11 pages.
In the U.S. Patent and Trademark Office, Office Action in re: U.S. Appl. No. 11/478,970, dated Jan. 25, 2008, 9 pages.
In the U.S. Patent and Trademark Office, Office Action in re: U.S. Appl. No. 12/268,051, dated Jan. 22, 2010, 8 pages.
In the U.S. Patent and Trademark Office, Requirement for Restriction/Election in re: U.S. Appl. No. 12/268,051, dated Jun. 16, 2009, 6 pages.
In the U.S. Patent and Trademark Office, Final Office Action in re: U.S. Appl. No. 11/135,693, dated Jan. 9, 2008, 10 pages.
In the U.S. Patent and Trademark Office, Office Action in re: U.S. Appl. No. 11/135,693, dated Apr. 23, 2007, 11 pages.
In the U.S. Patent and Trademark Office, Requirement for Restriction/Election in re: U.S. Appl. No. 11/135,693, dated Jan. 9, 2007, 6 pages.
In the U.S. Patent and Trademark Office, Final Office Action in re: U.S. Appl. No. 12/250,328, dated Sep. 3, 2010, 7 pages.
In the U.S. Patent and Trademark Office, Office Action in re: U.S. Appl. No. 12/250,328, dated Aug. 3, 2009, 7 pages.
In the U.S. Patent and Trademark Office, Final Office Action in re: U.S. Appl. No. 11/135,675, dated Apr. 11, 2008, 9 pages.
In the U.S. Patent and Trademark Office, Office Action in re: U.S. Appl. No. 11/135,675, dated Sep. 5, 2007, 7 pages.
In the U.S. Patent and Trademark Office, Requirement for Restriction/Election in re: U.S. Appl. No. 11/135,675, dated May 11, 2007, 8 pages.
In the U.S. Patent and Trademark Office, Office Action in re: U.S. Appl. No. 12/250,332, dated Sep. 1, 2009, 5 pages.
In the U.S. Patent and Trademark Office, Final Office Action in re: U.S. Appl. No. 11/135,694, dated Apr. 11, 2008, 7 pages.
In the U.S. Patent and Trademark Office, Office Action in re: U.S. Appl. No. 11/135,694, dated Sep. 5, 2007, 5 pages.
In the U.S. Patent and Trademark Office, Requirement for Restriction/Election in re: U.S. Appl. No. 11/135,694, dated Jul. 5, 2007, 6 pages.
In the U.S. Patent and Trademark Office, Final Office Action in re: U.S. Appl. No. 10/697,563, dated Apr. 15, 2009, 9 pages.
In the U.S. Patent and Trademark Office, Office Action in re: U.S. Appl. No. 10/697,563, dated Jun. 27, 2008, 11 pages.
In the U.S. Patent and Trademark Office, Office Action in re: U.S. Appl. No. 10/697,563, dated Nov. 16, 2007, 13 pages.
In the U.S. Patent and Trademark Office, Office Action in re: U.S. Appl. No. 10/697,563, dated Jan. 25, 2007, 11 pages.
In the U.S. Patent and Trademark Office, Final Office Action in re: U.S. Appl. No. 10/697,563, dated Aug. 8, 2005, 7 pages.
In the U.S. Patent and Trademark Office, Office Action in re: U.S. Appl. No. 10/697,563, dated Feb. 24, 2005, 7 pages.
In the U.S. Patent and Trademark Office, Requirement for Restriction/Election in re: U.S. Appl. No. 10/697,563, dated Jul. 16, 2004, 4 pages.
In the U.S. Patent and Trademark Office, Final Office Action in re: U.S. Appl. No. 11/102,278, dated Jan. 29, 2010, 11 pages.
In the U.S. Patent and Trademark Office, Office Action in re: U.S. Appl. No. 11/102,278, dated Apr. 15, 2009, 7 pages.
In the U.S. Patent and Trademark Office, Final Office Action in re: U.S. Appl. No. 11/102,278, dated Aug. 8, 2008, 7 pages.
In the U.S. Patent and Trademark Office, Office Action in re: U.S. Appl. No. 11/102,278, dated Dec. 21, 2007, 11 pages.
In the U.S. Patent and Trademark Office, Office Action in re: U.S. Appl. No. 11/102,278, dated Apr. 23, 2007, 8 pages.
In the U.S. Patent and Trademark Office, Office Action in re: U.S. Appl. No. 11/102,278, dated Dec. 21, 2006, 5 pages.
In the U.S. Patent and Trademark Office, Final Office Action in re: U.S. Appl. No. 12/250,334, dated Jun. 11, 2010, 6 pages.
In the U.S. Patent and Trademark Office, Office Action in re: U.S. Appl. No. 12/250,334, dated Sep. 3, 2009, 10 pages.
In the U.S. Patent and Trademark Office, Final Office Action in re: U.S. Appl. No. 11/595,558, dated Apr. 14, 2008, 9 pages.
In the U.S. Patent and Trademark Office, Requirement for Restriction/Election in re: U.S. Appl. No. 13/919,589, dated Mar. 7, 2014, 9 pages.
In the U.S. Patent and Trademark Office, Office Action in re: U.S. Appl. No. 13/919,589, dated Jun. 24, 2014, 11 pages.
In the U.S. Patent and Trademark Office, Notice of Allowance in re: U.S. Appl. No. 13/919,589, dated May 27, 2015, 8 pages.
Berga et al., The Merck Manual 2nd Home Edition, Section 12 Disorders of Nutrition and Metabolism, 2003; pp. 922, 926.
Bergman, "Mechanisms of anticancer drug resistance," Vet Clin Small Anim, 2003; 33, pp. 651-667.
Lee et al., "Anti-Atherogenic Effect of Citrus Flavonoids, Naringin and Naringenin, Associated with Hepatic ACAT and Aortic VCAM-1 and MCP-1 in High Cholesterol-Fed Rabbits," Biochem. Biophys. Res. Comm, 2001: 284, pp. 681-688.
Block et al., "Fruit Vegetables, and Cancer Prevention: A Review of the Epidemiological Evidence", Nutrition and Cancer, 1992: 18(1), pp. 1-29.
Boring et al., "Cancer Statisitcs, 1993", A Cancer Journal for Clinicians, Jan./Feb. 1993: 43, pp. 7-26.
Borradaile et al., "Regulation of HepG2 Cell Apolipoprotein B Metabolism by the Citrus Flavanones Hesperitin and Naringenin.", Lipids, 1999: 34, pp. 591-598.
Borradaile et al., "Regulatory effects of citrus flavonoids on apo B metabolism in HepG2 cells,", FASEB Journal, Mar. 17, 1998: 12(4), p. A207.
Bracke et al, "Influence of Tangeretin on Tamoxifen's Therapeutic Benefit in Mammary Cancerr," J. Natl. Cancer Inst., 1999: 91(4), pp. 345-349.
Bracke et al., "Citrus flavonoid effect on tumor invasions and metastasis the citrus flavonoid tangeritin may inhibit the processes that shorten the life expectancy of tumor-bearing patients", Food Technology, Nov. 1, 1994: 48(11), pp. 121-124.
Calomme et al., "Inhibition of Bacterial Mutagenesis by Citris Flavonoids," Planta Med., Jun. 1996: 62, pp. 222-226.
Cao et al., "Acyl Coenzyme A Preference of Diacylglycerol Acyltransferase from the Maturing Seeds of *Cuphea*, Maize, Rapeseed, and Canola," Plant Physoil., 1987; 84, pp. 762-765.
Carroll et al., "In Vitro Inhibition of Proliferation of MDA-MB-435 Human Breast Cancer Cells by Combinations of Tocotrienols and Flavonoids," FASEB J., 1995: 9(4), p. A868.
Carroll et al., "Dietary Fatty Acids, Tocotrienols, and Cancer," Journal of Food Lipids, 1998: 5, pp. 141-147.
Carroll et al.. "Anticancer properties of flavonoids, with emphasis on citrus flavonoids", Antioxid. Health Dis., 1998: 7, pp. 437-446.
Carroll, "Lipids and Carcinogenesis," J. Env. Pathol. Tox., 1980: 3, pp. 253-271.
Castelli et al., "Incidence of Coronary Heart Disease and Lipoprotein Choleesterol Levels", JAMA, 1986: 256, pp. 2835-2838.
Charleux, Beta-Carotene, Vitamin C, and Vitamin E: The Protective Micronutrients,: Nutr. Rev., 1996: 54(11), pp. S109-S114.
Choi et al., "Antihyperlipidemic Effect of Flavonoids From *Prunus davidiana*," J. Nat. Prod., 1991: 54 (1), pp. 218-224.
Chun et al, "Update on the biology and management of canine osteosarcoma," Vet Clin Small Anim., 2003; 33, pp. 491-516.
Cook et al., "Flavonoids-Chemistry, metabolism, cardioprotective effects, and dietary sources", Nutritional Biochemistry, 1996: 77, pp. 67-76.
Croteau et al., "Seed Lipids The American Cranberry (*Vaccinium macrocarpon*)", Phytochemistry, 1969: 8, pp. 2219-2222.
Crowell et al., " Monoterpenes in breast cancer chemoprevention", Breast Cancer Res. Tr., Nov. 1997: 46(2-3), pp. 191-197.
Cummings et al., "Adjuvant Tamoxifen Treatment of Elderly Women with Stage II Breast Cancer", Annals of Internal Medicine, 1985: 103, pp. 324-329.
Dashiti et al., "Effects of Oleate and Insulin on the Production Rates and Cellular Mrna Concentrations of Apolipoproteins in HepG2 Cells". J. Lipid Res., 1989: 30, pp. 1365-1373.
de Jong et al., "Metabolic effect of pant sterols and stanols (Review)", Journal of Nutritional Biochemistry, 2003: 14, pp. 362-369.

(56) References Cited

OTHER PUBLICATIONS

Definition of Rapeseed, [online], [retreived on Jul. 6, 2007]. Retreived from the Internet: <URL: http://en/wikipedia.org/wiki/Rapeseed>.

DeVita et al., "Combination Versus Single Agent Chemotherapy: A Review of the Basis for Selection of Drug Treatment of Cancer," Cancer, 1975: 35, pp. 98-110.

Dreyer et al., "Flavonoids of citrus-VIII synthesis of limocitrol, limocitrin and spinacetin". Tetrahedron, 1964: 20, pp. 2977-2983.

Economic Research Service, USDA, "Crambe, Industrial Rapeseed, and Tung Provide Valuable Oils," Industrial Uses/IUS-6, 1996, pp. 17-23.

Formica et al., "Review of the Biology of Quercetin and Related Bioflavonoids," Food Chem. Toxicol., 1995: 33(12), pp. 1061-1080.

Frankel et al., "Inhibition of oxidation of two LDL samples (a and b) by wine phenolics (µmol/L)," Lancet, 1993: 341, pp. 1103-1104.

Goad et al., "Analysis of Sterols," Springer publisher, 1997. Table of Contents and Preface retrieved from the internet, [online], [retrieved on Apr. 14, 2015]. Retrieved from the Internet: <URL: http://www.amazon.com/Analysis-Sterols-J-Goad/dp/07514020303>.

Gryglewski et al., "On the Mechanism of Antithrombotic Action of Flavonoids", Biochem. Pharmacology, 1987: 36, pp. 317-322.

Guthrie et al., "Abstract 1907: combined effect of palm oil tocotrienols, flavonoids, and tamoxifen on the proliferation of estrogen receptor-postive MCF-7 human breats cancer cells", Proceedings of the Amercian Association for Cancer Research, Mar. 1996: 37, p. 280.

Guthrie et al., "In vitro studies on anti-cancer and cholesterol-lowring activities of citrus flavonoids and ilinonoids", FASEB J. FED of American Soc. For Exp. Biol., 2000: 14, p. A563.

Guthrie et al., "Inhibition of Mammary Cancer by Citrus Flavonoids", Advances in Experimental Medicine and Biology, 1998: 439, pp. 227-236.

Guthrie et al., "Palm oil tocotrienols and plant flavonoids act synergistically with each other and with Tamoxifen in inhibiting proliferation and growth of estrogen receptor-negative MDA-MB-435 and positive MCF-7 human breast cancer cells in culture", Asia Pacific J. Clin. Nutr, 1997: 6(1), pp. 41-45.

Guthrie et al., "Effects of Palm Oil Tocotrienols, Flavonoids and Tamoxifen on Prolifemtion of MDA-MB-435 and MCF-7 Human Breast Cancer Cells," Proc. Am. Inst. Cancer Res., 1996: Abs. #8.

Harborne, "The Flavonoids", 1994, Chapman Hall, London, UK, pp. 308, 359, 370, 383.

Hardman and Limbird eds., Goodman and Gilman's The Pharmacological Basis of Therapeutics, McGraw-Hill, 1996: 9th Ed. see p. 1510.

Hasegawa et al., "Biochemistry and Biological Functions of Citrus Limonoids", Food Rev. Int., 1996: 12(4), pp. 413-435.

Hasegawa et al., "Biochemistry of Citrus Limonoids and Their Anticarcinogenic Activity," Food Phyochemicals for Cancer Prevention I, eds M-t. Huang et al., American Chemical Society, 1994, pp. 198-207.

Hatley et al., "Increased production of 12/15 lipoxytgenase eicosanoids accelerates moocyte/endothelial interations in diabetic db/db mice," J Boil Chem, 2003; 278(28), 25369-75, printed pp. 1 and 2.

Hawley's Condensed Chemical Dictionary, 13th Edition, 1997, p. 204.

Heinonen et al., "Antioxidant Activity of Berry and Fruit Wines and Liquors", Journal of Agricutlural and Food Chemistry, 1998: 46(1), pp. 25-31.

Hertog et al., "Content of Potentially Anticarcinogenic Flavonoids of 28 Vegetables and 9 Fruits Commonly consumed in The Netherlands", J. Agric Food Chem., 1992: 40, pp. 2379-2383.

Hertog et al., "Content of Potentially Anticarcinogenic Flavonoids of Tea Infusions, Wines, and Fruit Juices", J. Agric Food Chem., 1993: 41, pp. 1242-1246.

Hertog et al., "Dietary antioxidant flavonoids and risk of coronary heart disease: the Zutphen Elderly Study," Lancet, 1993: 324, pp. 1007-1011.

Hirano et al. "Citrus flavone tangeretin inhibits leukaemic HL-60 cell growth partially through inducation of apoptosis with less cytotoxicity on normal lymphocytes," Br. J. Cancer, 1995: 72(6), pp. 1380-1388.

Ho et al., "Bioactive hydroxylated polymethoxyflavones from citrus processing by-products", 232nd ACS National Meeting, Sep. 10-14, 2006, Abstract of papers.

Horowitz et al., Flavonoids of Citrus V. Structure of Limocitrin, J. Org. Chem., 1961: 26, pp. 2899-2902.

Horowitz et al., "Flavonoids of Citrus. IV. Isolation of Same Aglycones form the Lemon (Citrus limon)," J. Org. Chem., 1960: 25, pp. 2183-2187.

Horowitz et al., "Life event questionnaires for measuring presumptive stress," Psychosom Med., 1977: 39(6), pp. 413-431.

Hunt et al., "Hyperlipoproteinaemia and atherosclerosis in rabbits fed low-level cholesterol and lecithin," British J. of Experimental Pathology, 1985: 66, pp. 35-46.

International Search Report for PCT/CA02/000662, dated Oct. 4, 2002.

International Search Report for PCT/IB01/00256, dated Jun. 6, 2001.

International Search Report for PCT/IB05/000929, dated Oct. 14, 2005.

International Search Report for PCT/IB05/001420, dated Nov. 7, 2005.

International Search Report for PCT/IB05/001424, dated Oct. 11, 2005.

International Search Report for PCT/IB05/001427, dated Oct. 11, 2005.

International Search Report for PCT/IB06/004220, dated Oct. 17, 2007.

International Search Report for PCT/IB07/002525, dated Feb. 14, 2008.

International Search Report for PCT/IB07/003174, dated May 16, 2008.

International Search Report for PCT/IB14/001069, dated Oct. 14, 2014.

International Search Report for PCT/IB2006/003020, dated Jun. 20, 2007.

International Search Report for PCT/IB98/001721, dated May 7, 1999.

International Search Report for PCT/US01/008395, dated Aug. 14, 2001.

International Search Report for PCT/US06/025588, dated Mar. 28, 2007.

Iwase et al., "Inhibitory effect of Flavonoids from Citrus plants on Epstein-Barr virus activation and two-stage carcinogenesis of skin tumors" Cancer Letters, 2000: 154, pp. 101-105.

Iwata et al., "The Effect of Various Phospholipids on Plasma Lipoproteins and Liver Lipids in Hypercholesterolemic Rats," J. Nutr. Sci. Vitaminol., 1993: 39, pp. 63-71.

Javitt, "Hep G2 cells as a resource for metabolic studies: lipoprotein, cholesterol, and bile acids", FASEB Journal, 1990: 4, pp. 161-168.

Jones et al., "Phytosterrols in low- and nonfat beverages as part of a controlled diet fail to lower plasma lipid levels," J. Lipid Res., 2003: 44, pp. 1713-1719.

Kamb, "What's wrong with our cancer models?" Nature Reviews: Drug Discovery, 2005: 4, pp. 161-165.

Kandaswami et al., "Antiproliferative effects of citrus flavonoids on a human squamous cell carcinoma in vitro," Cancer Letters, 1991:56, pp. 147-152.

Kasim-Karakas et al., "Effects of Dietary Carbohydrates on Glucose and Lipid Metabolism in Golden Syrian Hamsters.", J. Lab. Clin. Med., 1996: 128, pp. 208-213.

Katsanidis et al., Free Radical Biology & Medicine, Dec. 1999: 27(11-12), pp. 1137-1140 (abstract only).

Kawai, "Anticancer effect of citrus essential oil", Aroma Res., 2003: 4(2), pp. 8-15.

(56) References Cited

OTHER PUBLICATIONS

Kawaii et al., Bioscience, Biotechnology, and Biochemistry, May 1999: 63, pp. 896-899.
Keli et al., "Dietary Flavonoids, Antioxidant Vitamins, and Incidence of Stroke", Arch. Inter. Med., 1996: 154, pp. 637-642.
Kerckhoffs et al., "Effects on the human serum lipoprotein profile of beta-glucan, soy protein and isoflavones, plant sterols and stanols, garlic and tocotrienols.", J. Nutr., Sep. 2002: 132(9), pp. 2494-2505.
Kim et al., "Inhibition of Alpha-glucosidase and Amylase by Luteolin, a Flavonoid," Biosci. Biotechnol. Biochem., 2000: 64(11), pp. 2458-2461.
Kim et al., "Tangeretin stimulates glucose uptake via regulation of AMPK signaling pathways in C2C12 myotubes and improves glucose tolerance in high-fat diet-induced obese mice," Molecular and Cellular Endocrinology, 2012: 358, pp. 127-134.
Klein, "Defense of Reactions in Action", Immunology, The Science of Self-NonSelf Discrimination, 1982: Chapter 14, pp. 577-584.
Kuhnau, "The Flavonoids. A class of semi-essential food components: Their role in human nutrition.", World Review of Nutrition and Diet, 1976: 24, pp. 117-191.
Kurioka et al., "Reverse Correlation Between Urine Nitric Oxide Metabolites and Insulin Resistance in Patients with Type 2 Diabetes Mellitus.", Endoc. J., 2000: 47, pp. 77-81.
Kurowska et al., "Regulatory Effects of Tangeritin, A Flavonoid from Tangerines, and Limonin, A Liminoid from Citrus, on Apo B Metabolism in HepG2 Cells", FASEB Journal, 2000, p. A298.
Kurowska et al., "Role of tocotrienols from palm oil in regulation of apo B metabolism in HEPG2 cells.", FASEB Journal, Mar. 12, 1999: 13(4)(Part 1), p. A562.
Kurowska et al., "Cardioprotective Effect s of Supplementation with Citrus Phytochemicals and Tocotrienols in Subjects with Moderate Hypercholesterolemia", FASEB Journal, Apr. 2004: 18(4-5), pp. A858.
Kurowska et al., "Hypolipidemic activities of tangeritin a flavonoid from tangerine in vitro and in vivo", FASEB J., 2001:15, p. A395 (abstract).
Kurowska et al., "Hypolipidemic effects and absorption of citrus polymethoxylated flavones in hamsters with diet-induced hypercholesterolemia" J Agr. Food Chem, 2004: 52, pp. 2879-2886.
Kurowska et al., "Regulation of apo B production in HepG2 cells by citrus liminoids", ACS Symp. Ser., 2000: 758, pp. 175-184.
Kurowska et al., "Regulation of apo B production in HepG2 cells by citrus liminoids", American Chemical Socitey abstract of papers, Mar. 21-25, 1999: 217(1-2), p. AGFD 57.
Kurowska et al., "Regulation of lipoprotein metabolism in HEPG2 cells by citrus flavonoids", American Chemical Society—Abstracts of Papers 2000: p. 219.
Kurowska et al., "Tangeritin a citrus flavonoid reduces metabolic abnormalities associated with insulin resistance", FASEB J., Mar. 20, 2002: 16(4), p. A648 (abstract).
Kurowska et al., "Essential Amino Acids in Relation to Hypercholesterolemia Induced in Rabbits by Dietary Casein1," J Nutr., 1990: 120, pp. 831-836.
Kwiterovich et al., "Prevalence of Hyperapobetalipoproteinemia and Other Lipoprotein Phenotypes in Men (Aged <50 Years) and Women (<60 Years) with Coronary Artery Disease," The American J. of Cardiology, 1993: 71(8), pp. 631-639.
Lam et al., "Citrus liminoid reduction of chemically induced tumorigenesis bitter compounds found in citrus fruits may be useful cancer-preventive agents", Food Technology, Nov. 1, 1994: 48(11), pp. 104-108.
Lam et al., "Inhibition of Chemically Induced Carcinogenesis by Citrus Limonoids," Food Phytochemicals for Cancer Prevention I: Fruits and Vegetables, eds M-t. Huang et al., ACS Symposium Series, 1994: pp. 209-219.
Lam et al., "Inhibition of Benso[a]pyrene-Induced Forestomach Neoplasia in Mice by Citrus Limonoids," Nutr. Cancer, Jan. 1989: 12(1), pp. 43-47.
Lee et al., "Nobiletin improves hyperglycemia and insulin resistance in obese diabetic ob/ob mice," Biochemical Pharmacology, 2010: 79, pp. 1674-1683.
Li et al. "Nitric Oxide in the Pathogenesis of Vascular Disease", J. Pathol., 2000: 190, pp. 244-254.
Mak et al., "Isolation of Anti-Leukemia Compounds from Citrus Reticulata," Life Sciences, 1996: 58(15), pp. 1269-1276.
Malterud et al., "Inhibitors of 15-lipoxygenase from orange peel", J Agric. Food Chem., Nov. 2000: 49(11) pp. 5576-5580 (abstract only).
Manthey et al., "Antiproliferative activities of synthetic derivatives of methoxylated flavones from citrus," 222nd ACS National Meeting, Aug. 26-30, 2001, Abstract of papers.
Manthey et al., "Biological properties of citrus flavanoids pertaining to cancer and inflammation", Curr. Med. Chem., 2001: 8(2), pp. 135-153.
Marthey et al., "Flavonoids in the Living System", 1996, Plenum Press, New York, USA, pp. 152-154, 165-173, 191-195, 221-225.
McGill et al., "Relationship of blood cholesterol and apoprotein B levels to angiographically defined coronary artery disease in young males," Coron. Artery Dis., 1993: 4(3), pp. 261-270.
Merck Research Laboratories, "The Merck manual of diagnosis and therapy", Merck Research Laboratories, 1999: pp. 166-167, Whitehouse Sation, NJ, USA.
Middleton et al., "The effects of plant flavonoids on mammalian cells: implications for inflammation, heart disease, and cancer," Pharmacol Rev., 2000: 52(4), pp. 673-751.
Miller et al., "Citrus liminoids as inhibitors of oral carcinogenesis seven citrus compounds were tested for their cancer-preventive activity", Food Technology, Nov. 1, 1994: 48(11), pp. 110-112, 114.
Miller et al., "The effect of citrus limonoids on hamster buccal puch carcinogenesis," Carcinogenesis, Aug. 1989: 10(8), pp. 1535-1537.
Miller et al., "Inhibition of Hamster Buccal Pouch Carcinogenesis by Limonin 17-β-D-Glucopyranoside," Nutr. Cancer, Jan. 1992: 17(1), pp. 1-7.
Minhajuddin, "Hypolipidemic and antioxidant properties of tocotrienol rich fraction isolated from rice bran oil in experimentally induced hyperlipidemic rats," Food Chem. Toxicol., 2005: 43, pp. 747-753.
Miyata et al., "Regulation of adipocytokine secretion and adipocyte hypertrophy by polymethoxyflavonoids, nobiletin and tangeretin," Life Sciences, 2011: 88, pp. 613-618.
Moghadasian et al., "Effects of Dietary Phytosterols and Cholesterol Metabolism and Aterosclerosis: Clinical and Experimental Evidence", The American Journal of Medicine, 1999: 107, pp. 588-594.
Monforte et al., "Biological effects of hesperidin, a citrus flavonoid, (Note II): Hypolipidemic activity on experimental hypercholesterolemia in rat", II Farmaco, Sep. 9, 1995: 50(9), pp. 595-599.
Mordenti, "Man versus Beast: Pharmacokinetic Scaling in Mammals", J. of Pharm. Science, Nov. 1986: 75(11), pp. 1028-1040.
Moreau et al. "Physterols, phytostanols, and their conjugates in foods: structural diversity, quantitative analysis, and health-promoting uses", Progress of Lipid Research, 2002: 41, pp. 457-500.
Morley et al., "Tangeretin and nobiletin induce G1 cell cycle arrest but not apoptosis in human breast and colon cancer cells," Cancer Letters, 2007: 251, pp. 168-178.
Mortensen et al., "Relative stability of caotenoid radical cations and homologue tocopheroxyl radicals. A realt time kinetic study of antioxidant heirarchy", Febs Letters—Elsevier Science Publishers, Nov. 1997: 417(3), pp. 261-266.
Mulvihill et al., "Nobiletin Attenuates VLDL Overproduction, Dyslipidemia, and Atherosclerosis in Mice With Diet-Induced Insulin Resistance," Diabetes, May 2011: 60, pp. 1446-1457.
Natarajan et al., "Lipid inflammatory mediators in diabetic vac\scular disease", Arteriosclerosis, Thrombosis and Vascular Biology, 2004: 24(9), p. 1542.
Nydahl et al., "Similar Effects of Rapeseed Oil (Canola Oil) and Olive Oil in a Lipid-Lowering Diet for Patients with Hyperlipoproteinemia," J. of the American College of Nutrition, 1995; 14(6), pp. 643-651.

(56) References Cited

OTHER PUBLICATIONS

O'Brien et al., "Influence of Dietary Egg and Soybean Phospholipids and Triacylglycerols on Human Serum Lipoproteins," Lipids, 1993: 28(1), pp. 7-12.
Oshida et al., "Nitric Oxide Decreases Insulin Resistance Induced by High-Fructose Feeding", Horm. Metab. Res., 2000: 32, pp. 339-342.
Ostlund et al., "Sitostanol administered in lecithin micelles potently reduces cholesterol absorption in humansl-3," Am. J. of Clinical Nutrition, 1999: 70, pp. 826-831.
Parker et al., "Tocotrienols Regulate Cholesterol Production in Mammalian Cells by Post-transcriptional Suppression of 3-Hydroxy-3-methylglutaryl-Coenzyme A Reductase*," J Biol. Chem., 1993: 268(16), pp. 11230-11238.
Pearce et al., "Hypocholesterolemic Activity of Synthetic and Natural Tocotrienols," J. Med. Chem., 1992: 35, pp. 3595-3606.
Polichetti et al., "Stimulation of the apo Al-high density lipoprotein system by dietary soyabean lecithin in humans," J. of Nutritional Biochemistry, Nov. 1998: 9, pp. 659-664.
Priester and McKay, 1980.
Reddy et al., Chemoprevention of colon carcinogenesis by dietary perillyl alcohol, Cancer Res., Feb. 1, 1997: 57(3), pp. 420-425.
Remington's Pharmaceutical Sciences, 1985, 17th edition, Mack Publishing Co., Pennsylvania, USA, pp. 863-865.
Remington's The Science and Practice of Pharmacy, 2000, 20th edition, Lippincott Williams and Wilkins, pp. 743-747 and 858-863.
Report of the National Education Expert Panel on Detection, Evaluation, and Treatment of High Blood Cholesterol in Adults, Arch. Intern. Med., 1988: 148, 36.
Robbins, "Effect of flavonoids on survival time of rats fed thrombogenic of atherogenic regimes", J Atheroscler Res, 1967: 7(1), pp. 3-10.
Rosenthal, "Effectiveness of altering serum cholesterol levels without drugs", Baylor University Medical Center Proceedings, 2000: 13, pp. 351-355.
Rottiers, "Diabetese and Nutrition," Inform, 2000: 11, pp. 873-877.
Samochowiec et al., Atherosclerotic, 1976: 23(2), pp. 305-317 (abstract only).
Sattin et al., Family History and thhe Risk of Breast Cancer, JAMA, Apr. 5, 1985, 253(13), pp. 1908-1913.
Schatzkin et al., "Alcohol Consumption and Breas Cancer in the Epidemiologic Follow-up Study of the First National Health and Nutrition Examination Survey," N. Engl. J. Med., 1987: 316(19), p. 1169-1173.
Silalahi, "Anticancer and health protective properties of citrus fruit components," Asia Pac J Clin Nutr., 2002: 11(1), 79-84.
Simons et al., "Treatment of Hypercholesterolaemia with Oral Lecithin*," Aust. N.Z. J. of Medicine, 1972: 7, pp. 262-266.
Sniderman et al., "Association of coronary atherosclerosis with hyperapobetalipoproteinemia [increased protein but normal cholesterol levels in human plasma low density (β) lipoproteins]," Proc. Natl. Acad. Sci., 1980: 77(1), pp. 604-608.
Stamler et al., "Is Relationship Between Serum Cholesterol and Risk of Premature Death From Coronary Heart Disease Continuous and Drradded?" JAMA, 1986: 256(20), pp. 2823-2828.
Steinmetz et al, "Vegetables, Fruit, and Cancer" I. Epidemiology, Cancer Causes Control, 1991: 2, pp. 325-357.
Steinmetz et al, "Vegetables, Fruit, and Cancer" II. Mechanisms, Cancer Causes Control, 1991: 2, pp. 427-442.
Sugino et al., "Antioxidative Activity of Egg Yolk Phospholipids," J Agric. Food Chem., 1997: 45, pp. 551-554.
Sugiyama et al., "Studies on the Differentiation Inducers of Myeloid Leukemic Cells from Citrus Species", Chem Pharm. Bull., 1993: 41(4), pp. 714-719.
Sun et al., "Acyl Coenzyme A Preference of the Glycerol Phosphate Pathway in the Microsomes from the Maturing Seeds of the Palm, Maize, and Rapeseed," Plant Physiol., 1988; 88, pp. 56-60.
Taghibiglou et al., "Mechanism of Hepatic Very Low Density Lipoprotein Overproduction in Insulin Resistance". J. Biol. Chem., 2000: 275, pp. 8416-8425.
Takanaga et al., "Polymethoxylated Flavones in Orange Juice are Inhibitors of P-glycoprotein but Not Cytochrome P450 3A4," J. of Pharmacology and Experiments Therapuetics, 1999: 293(4), pp. 230-236.
Tan et al., "Effect of a palm-oil-vitamin E concentrate on the serum and lipoprotein lipids in humans 1-3," J. Clin. Nutr., 1991: 53, pp. 1027S-1030S.
Tatum et al., "Six New Flavonoids From Citrus", Phytochemistry II, 1972: 11, pp. 2283-2288.
The Merck Manual of Diagnosis and Therapy, 16th Edition, Berkow and Fletcher, Merck & Co., Rahway, New Jersey, USA, 1992. (Table of Contents).
The New Zealand Medical Journal, Oct. 8, 2004: 117(1203).
Theriault et al., "Tocotrienol is the most effective vitamin E for reducing endothelial expression of adhesion molecules and adhesion to monocytes," Atherosclerosis, 2002: 160, pp. 21-30.
Theriault et al., "Tocotrienol: A Review of Its Therapeutic," Clin. Biochem., 1999: 32, pp. 309-319.
Tornvall et al., "Relation of Plasma Levels and Composition of Apolipoprotein B-Containing Lipoproteins to Angiographically Defined Coronary Artery Disease in Young Patients With Myocardial Infarction," Circulation, 1993: 88(5), pp. 2180-2189.
Toth et al., "The Good Cholesterol": High Density Lipoprotein, Circultion—Journal of the American Heart Association, 2005: 111, pp. 89-91.
Wang et al., "Antimicrobial Flavonoids from Psiadia trinervia and their Methylated and Acetylated Derivatives"., Phytochemistry, 1989: 23(9), pp. 2323-2327.
Wang et al., "Ellagic Acid Content in Small Fruits, Mayhaws, and Other Plants", Journal of Small Fruits and Viticulture, 1994: 2(4), pp. 39-49.
Whitman et al.. Atherosclerosis, Jan. 2005: 178(1), pp. 25-32 (abstract only).
Wilson et al., "Soy lecithin reduces plasma lipoprotein cholesterol and early atherogenesis in hypercholesterolemic monkeys and hamsters: beyond linoleate," Atherosclerosis, 1998: 140, pp. 147-153.
Wojcicki et al., "Clinical Evaluation of Lecithin as a Lipid-lowering Agent," Phytotherapy Research, 1995: 9, pp. 597-599.

* cited by examiner

Figure 1

Serum glucose concentrations over a 4-hour period following a 100g OGTT at baseline, week 12 and week 24 of supplementation with the composition of an embodiment of the present invention or placebo.

a) Composition - Completers b) Placebo - Completers

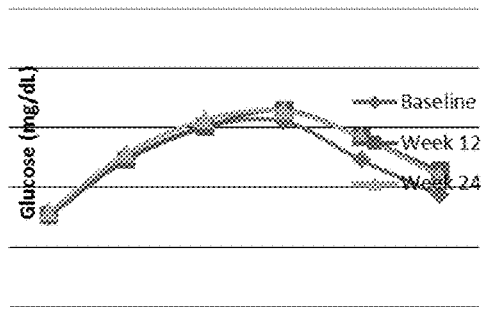
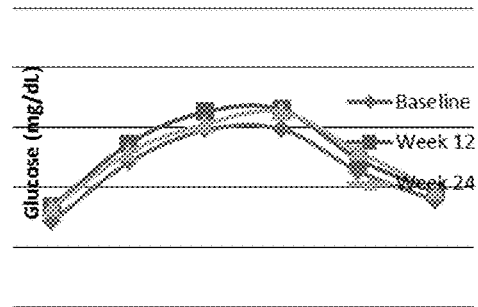

c) Composition - Completers with fasting glucose >100mg/dL, 2h post-prandial glucose >140mg/dL and HbA1c >7.0% d) Placebo - Completers with fasting glucose >100mg/dL, 2h post-prandial glucose >140mg/dL and HbA1c >7.0%

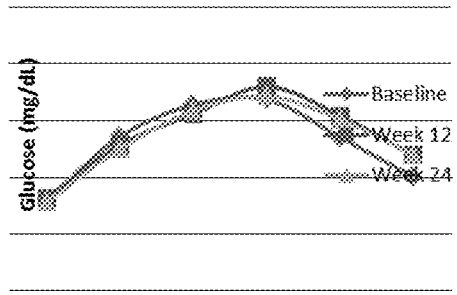
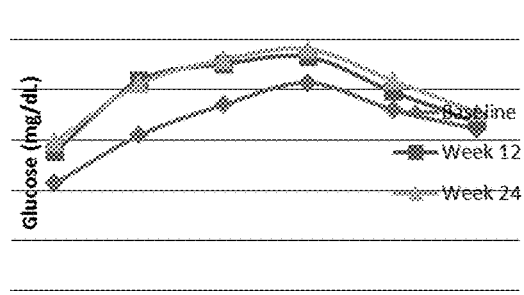

Figure 2
Serum insulin concentrations over a 4-hour period following a 100g OGTT at baseline, week 12 and week 24 of supplementation with the composition of an embodiment of the present invention or placebo.
a) Composition - Completers   b) Placebo - Completers
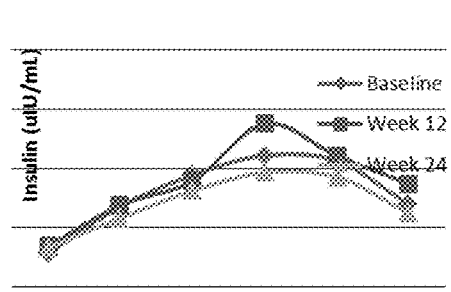 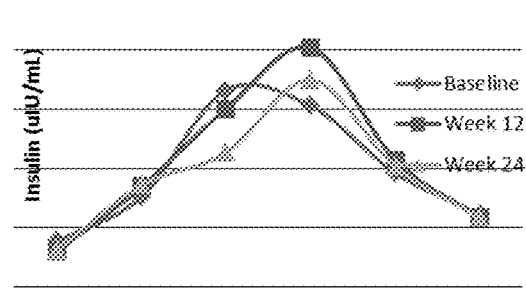

COMPOSITIONS AND METHODS FOR GLYCEMIC CONTROL OF SUBJECTS WITH IMPAIRED FASTING GLUCOSE

RELATED APPLICATIONS

This application is a continuation of U.S. patent application Ser. No. 13/919,589, filed Jun. 17, 2013, the contents of which is incorporated herein by reference in its entirety.

FIELD OF THE INVENTION

The present invention relates to compositions and methods for glycemic control of subjects with impaired fasting glucose, and, more specifically, to compositions and methods for improving glycemic control in subjects currently using conventional therapies.

BACKGROUND OF THE INVENTION

Metabolic syndrome, a condition thought to be caused by a combination of obesity, sedentary lifestyle, diet and genetics, has been found to increase the risk for cardiovascular disease and type 2 diabetes. The main characteristics of this syndrome are abdominal obesity, atherogenic dyslipidemia (elevated blood triglycerides, reduced HDL cholesterol), elevated blood pressure, insulin resistance (IR) (with or without glucose intolerance), prothrombotic and proinflammatory states and endothelial dysfunction. During the past 20 years, metabolic syndrome has become highly prevalent in North America, currently affecting an estimated 50% of the population older than 60 years.

Insulin resistance, one of the characteristics of metabolic syndrome, is defined as an impaired ability of insulin to stimulate glucose uptake and lipolysis and to modulate liver and muscle lipid metabolism. In animals and humans, insulin resistance syndrome leads to compensatory hyperinsulinemia and to various defects in lipid metabolism such as enhanced secretion of atherogenic, triacylglycerol-rich very low-density lipoproteins (VLDL), increased liberation of nonesterified fatty acids (NEFA) from adipose tissue and increased accumulation of triacylglycerols in the liver.

Current therapies in prevention and treatment of type 2 diabetes include diet and drugs. Dietary strategies designed to diminish the risk of heart disease associated with insulin resistance syndrome and type 2 diabetes are currently not well established. The most common approach is the recommendation to lower intake of total calories, especially fat and sugar, and to increase intake of fibers. The typical pharmacologic approach to the treatment of this disease focuses on drugs targeting obesity, glucose-lowering medications (e.g., metformin and acarbose) and more recently, insulin sensitizers such as PPAR-α and PPAR-γ activators, fibrates and thiazolidienodiones (TZDs). Unfortunately, therapies involving existing drugs have limited efficacy or tolerability and show significant side effects. There exists a need to provide a safe and effective method of treating metabolic syndrome and the diseases associated with it.

In the United States alone, approximately 24 million people suffer from diabetes with approximately 1.3 million being diagnosed with the disease each year. An aging population, rising obesity rates and an increasingly sedentary lifestyle have been attributed to the increase in incidence and prevalence. Furthermore, a rapid increase of type 2 diabetes in persons 30-39 years of age and in children and adolescents has been of special concern. Global prevalence rates are expected to increase from 6.4% and 285 million in 2010 to 7.7% and 439 million by 2030.

Clinical treatment goals for type 2 diabetes are directed towards lowering blood glucose levels to forestall diabetes related complications. More recently, the use of pharmacotherapies and their negative impact on cardiovascular risk have caused concern over available treatment modalities. An increased risk of myocardial ischemia has been identified with thiazolidinedione use, while earlier studies have linked Sulphonylureas to increased cardiovascular risk. Of further concern have been the contrasting outcomes of the ACCORD study which reported that lowering blood glucose to normal levels was associated with increased mortality, but the ADVANCE study did not report such findings. Such controversies in the results may suggest that treatment strategies for type 2 diabetes are not fully understood.

This begs the question if improving glycemia is sufficient to provide clinical merit in the treatment algorithm for diabetes. Currently, several therapeutic strategies include metformin in the management algorithm for type 2 diabetes with mono, di and tri therapy needing to be added to the algorithm. Therapies involving existing pharmaceuticals have limited efficacy or tolerability and show significant side effects. Many of the side effects of pharmaceuticals are thought to be associated with nutritional deficiencies caused by medications taken over a period of time ultimately resulting in a cascade of biochemical changes due to drug associated nutrient depletion. Unfortunately, long term treatment with metformin has been reported to cause vitamin B12 deficiencies. Despite the available treatment modalities, the risk of cardiovascular events has increased 2-4 fold in patients diagnosed with type 2 diabetes. As a patient's beta cell function declines, intensified treatment beyond the initial monotherapy regimen is required. The prevalence of obesity is also a concern in these patients and is thought to be a driver of cardiovascular events.

The "State of Diabetes in America" report on diabetes management evaluated current management strategies and found that, despite advances in diabetes care, blood sugar levels of millions of Americans were not controlled putting them at risk of diabetes related complications. It is possible that effective combination therapies that consist of pharmaceutical drugs and nutraceutical products may provide a new treatment algorithm that would be beneficial to diabetic patients who do not respond to drug therapy alone.

A 2005 report from the American Association of Clinical Endocrinologists (AACE) stated that 2 out of 3 Americans with type 2 diabetes did not achieve the AACE recommended blood sugar control goal of ≤6.5%. Nationally, an average of 67% of people with type 2 diabetes had blood sugar levels exceeding the AACE recommended goal. These numbers have a direct impact on cardiovascular disease risk factors for this population of subjects. NHANES 1999-2000 reported that only 7.3% of all adults diagnosed with type 2 diabetes were within acceptable range for the cardiovascular disease risk factors of HbA1c, blood pressure and total cholesterol. The American Association of Clinical Endocrinologists (AACE) acknowledges the importance of nutritional medicine in medical practice and in their guidelines identifies "complementary" or "integrative nutritionals" as products that may be used in combination with FDA approved therapies.

Needs exist for compositions and methods that provide anti-diabetic and anti-hyperlipidemia benefits to diabetic subjects currently on medication but not meeting ACCE and ADA recommended targets for blood glucose, HbA1c, blood pressure and total cholesterol.

SUMMARY OF THE INVENTION

It is therefore an object of the present invention to provide compositions and methods for glycemic control of subjects with impaired fasting glucose. The compositions and methods of the present invention may provide anti-diabetic and anti-hyperlipidemia benefits to diabetic subjects currently on medication but not meeting ACCE and ADA recommended targets for blood glucose, HbA1c, blood pressure and total cholesterol.

Embodiments of the present invention may include methods for administering an effective amount of a composition to a subject diagnosed with diabetes where the subject is currently taking one or more prescribed medications for control of diabetes but are not within one or more guidelines including: HbA1c≤7%; LDL-C≤100 mg/dL; total cholesterol≤200 mg/dL; and systolic blood pressure≤130 mmHg. After a predetermined period of supplementation with the composition, the subject may be within at least one of the one or more guidelines. The composition may include at least one limonoid, at least one flavonoid and at least one tocotrienol. The composition may include at least one polymethoxyflavone. The one or more prescribed medications may be metformin. The subject may be a human. The predetermined period of supplementation may be at least 12 weeks and/or at least 24 weeks.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIGS. 1a-1d are graphs showing serum glucose concentrations over a 4-hour period following a 100 g OGTT at baseline, week 12 and week 24 of supplementation with the composition of an embodiment of the present invention or placebo.

FIGS. 2a-2b are graphs showing serum insulin concentrations over a 4-hour period following a 100 g OGTT at baseline, week 12 and week 24 of supplementation with the composition of an embodiment of the present invention or placebo.

DETAILED DESCRIPTION OF THE INVENTION

The present invention relates to the use of compositions including at least one of limocitrin derivative, quercetin derivative, polymethoxyflavone, tocotrienol and mixtures thereof alone or in combination with at least one glycemic control drug for the treatment of subjects with impaired fasting glucose.

Limocitrin derivatives are a group of citrus-derived flavonoids that are naturally occurring in the plant or are chemically synthesized. 5-desmethylsinesetin is chemically synthesized form of sinensetin. Sinensetin occurs in trace levels in mandarin orange leaves, and in orange and mandarin peel. Flavonoids are polyphenolic compounds that occur ubiquitously in foods of plant origin. The major dietary sources of flavonoids are vegetables, fruits, and beverages such as tea and red wine. Flavonoids have been demonstrated to be the most potent dietary antioxidants and in light of the large dietary consumption, flavonoids make a major contribution to the antioxidant potential of the human diet. The main food sources of flavonols and flavones are black tea, onions, apples, herbs, and spices such as cloves and black pepper.

These compounds may include, but are not limited to, the following examples of limocitrin and quercetin derivatives: limocitrin-3,7,4'-trimethylether (5-hydroxy-3,7,8,3',4'-pentamethoxyflavone) limocitrin-3,5,7,4'-tetramethylether (3,5,7,8,3'4'-hexamethoxyflavone) limocitrin-3,5,7,4'-tetraethylether (8,3'-dimethoxy-3,5,7,4'-tetraethoxylfavone) limocitrin 3,7,4'-trimethylether-5-acetate quercetin tetramethylether (5-hydroxy-3,7,3',4'-tetramethoxyflavone) quercetin 3,5-dimethylether-7,3'4'-tribenzyl ether quercetin pentamethylether (3,5,7,3',4'-pentamethoxyflavone) quercetin-5,7,3',4'-tetramethylether-3-acetate quercetin-5,7,3',4'-tetramethylether (3-hydroxy-5,7,3',4'-tetramethoxyflavone).

Examples of naturally occurring polymethoxyflavones for the purposes of the present invention include, but are not limited to: 3,5,6,7,8,3',4'-heptamethoxflavone nobiletin (5,6,7,8,3',4'-hexamethoxyflavone) tangeretin (5,6,7,8,4'-pentametlioxyflavone) 5-desmethylnobiletin (5-hydroxy-6,7,8,3'4'-pentamethoxyflavone)tetra-O-methylisoscutellarein (5,7,8,4'-tetramethoxyflavone) 5-desmethylsinensetin (5-hydroxy-6,7,3',4'-tetramethoxyflavone) sinensetin (5,6,7,3',4'-pentamethoxyflavone).

Limocitrin occurs in the peel of lemon as limocitrin-3-O-glucoside, and can be produced from the 3-glycoside by enzymatic and acid hydrolysis or by a chemical synthesis procedure. Two limocitrin analogues, limocitrin 3,7,4'-trimethylether and limocitrin-3,5,6-4'-tetramethylether, also occur in orange peel. Several polymethoxyflavones were tested and found to be active as inhibitors of apolipoprotein B (apoB) production and had negligible cytotoxicity in the human liver carcinoma cell line HepG2. It has been shown that humans with coronary heart disease (CAD) have higher levels of apoB in their blood. ApoB concentrations also reflect the number of LDL, and VLDL (very low density lipoprotein) particles in arteries. Administering polymethoxylatedflavone of the invention to a mammal results in a reduction in the amount of substances in the blood which contribute to CAD, such as for example apoB, LDL, cholesterol, etc; preferably reduction of the serum, plasma, or whole blood concentration or in vivo amounts of these substances. Preferably, the concentration or in vivo amount of these substances is reduced to normal levels typically found in such a mammal. Also, preferably, the polymethoxylatedflavone of the present invention are administered in amounts which produce little or no cytotoxicity, more preferably where no cytotoxicity is produced.

By way of definition, a polymethoxylatedflavone is a flavone substituted with methoxy groups, preferably at least 2, more preferably at least 3, more preferably at least 4, more preferably 4-8, and most preferably 4-7 methoxy groups and optionally substituted by one or more hydroxy groups, preferably 1-3, and more preferably 1-2 hydroxy groups.

Four compounds of the present invention were synthesized from the lemon flavonoid limocitrin (3',8-dimethox-3,5,7,4'-tetrahydroxyflavone) for use in the present invention: limocitrin-3,7,4'-trimethylether (5-hydroxy-3,7,8,3',4'- pentamethoxyflavone); limocitrin-3,5,7,4'-tetramethylether (3,5,7,8,3'4'-hexamethoxyflavone); and limocitrin-3,7,4'-trimethylether-5-acetate.

A number of methoxylated flavones, most of which occur naturally in citrus, have been found to be useful in the present invention. Also included are substituted derivatives of quercetin. The compounds in these groups include 5-desmetlhymobiletin (5-hydroxy-6,7,8,3',4'-pentamethoxyflavone); tetra-O-methylisoscutellarein (5,7,8,4'-tetramethoxyflavone); 3,5,6,7,8,3',4'-heptamethoxyflavone; nobiletin (5,6,7,8,3',4'-hexamethoxyflavone); tangeretin (5,6,7,8,4'-pentamethoxyflavone); sinensetin (5,6,7,3',4'-pentamethoxyflavone); 5-desmethylsinensetin (5-hydroxy-6,7,3',4'-tetramethoxyflavone); quercetin tetramethylether (5-hydroxy-3,7,3',4'-tetramethoxyflavone); quercetin 3,5-dimethylether-7,3',4'-tribenzylether; quercetin pentamethyl ether (3,5,7,3',4'-pentamethoxyflavone); quercetin-5,7,3',4'-tetramethylether-3-acetate; quercetin-5,7,3',4'-tetramethylether (3-hydroxy-5,7,3',4'-tetramethoxyflavone).

Examples of tocotrienol compounds useful in the present invention include, but are not limited to, are alpha-tocotrienol, gamma-tocotrienol, delta-tocotrienol, and mixtures thereof.

The methods of the present invention may be administered to any mammal. Most preferably, the polymethoxylatedflavone useful in the methods of the present invention are administered to humans.

In another aspect of the present invention, the polymethoxylatedflavone may be formulated into a pharmaceutical preparation by a conventional method usually employed in the art.

Dosages for the compositions of the present invention may be formulated into pharmaceutical preparations for administration to mammals.

Many of the limocitrin derivatives, quercetin derivatives, naturally-occurring polymethoxyflavones, tocotrienol compounds and mixtures thereof may be provided as compounds with pharmaceutically compatible counterions, a form in which they may be soluble. Counterions for the purposes of this invention include, for example, hydrophilic and hydrophobic agents.

The polymethoxylatedflavone can be administered by a variety of routes, including oral, transdermal, rectal, intrarticular, intravenous, and intramuscular introduction. However, it should be understood that the amount of the polymethoxylatedflavone actually administered ought to be determined in light of various relavent factors including the condition to be treated, the chosen route of administration, the age and weight of the individual patient, and the severity of the patient's condition, and therefore, the doses given herein should not be construed to limit the scope of the invention in any way. The polymethoxylatedflavone useful in the present invention may be administered in a pharmaceutically or physiologically acceptable carrier. The pharmaceutically or physiologically acceptable carrier is any solvent with which the polymethoxylatedflavone is compatible and which is nontoxic to individuals treated at the amounts administered. A variety of delivery systems for pharmacological compositions may be employed including, but not limited to, liposomes and emulsions. The pharmaceutical compositions also may comprise suitable solid or gel phase carriers or excipients. Examples of excipients include, but are not limited to, calcium carbonate, calcium phosphate, various sugars, starches, cellulose derivatives, gelatin, and polymers such as polyethylene glycols.

Formulations suitable for oral administration include liquid solutions of the active compound or compounds dissolved in a diluent such as, for example, saline, water, PEG 400; solid preparations such as capsules or tablets, each containing a predetermined amount of the active agent as solids, granules, gelatins, suspensions, and/or emulsions.

Formulations suitable for parenteral administration include aqueous and non-aqueous isotonic sterile solutions which contain buffers, antioxidants, and preservatives. The formulations may be in unit dose or multi-dose containers.

Dosages administered are any effective amount of a polymethoxylatedflavone which will, when given for the treatment, prophylactically or therapeutically, reduce or prevent cardiovascular diseases by reducing levels of substances which contribute to cardiovascular diseases to normal or near normal levels in the blood or in vivo. By way of definition substances which contribute to cardiovascular diseases, include but are not limited to apoprotein B, low density lipoproteins, very low density lipoproteins, cholesterol, etc.

For local administration, the composition can be administered by injection directly into a tissue, often in a depot or sustained release formulation.

Flavonoids

Flavonoids are polyphenolic compounds that are found in plant foods, especially in oranges, grapefruits and tangerines. Polymethoxyflavones (PMFs) are flavonoid compounds having multiple methoxy substituents. Various beneficial effects of flavonoids are described in U.S. Pat. Nos. 6,251,400 and 6,239,114 and in PCT Publication Number WO 01/70029, the disclosures of which are hereby incorporated by reference in their entireties. Other beneficial effects of flavonoid derivatives are discussed in U.S. Pat. Nos. 4,591,600; 5,855,892; and 6,096,364, the disclosures of which are also hereby incorporated by reference in their entireties.

The flavonoids present in citrus juices such as orange and grapefruit include, but are not limited to, hesperetin and naringenin respectively.

Limonoids

Limonoids are a group of chemically related triterpene derivatives found in the Rutaceae and Meliaceae families. Limonoids are among the bitter principles found in citrus fruits such as lemons, lime, orange and grapefruit. They are also present as glucose derivatives in mature fruit tissues and seed, and are one of the major secondary metabolites present in citrus.

Citrus fruit tissues and byproducts of juice processing such as peels and molasses are sources of limonoid glucosides and citrus seed contain high concentrations of both limonoid aglycones and glucosides. Limonoid aglycones in the fruit tissues gradually disappear during the late stages of fruit growth and maturation.

Thirty-eight limonoid aglycones have been isolated from citrus. The limonoids are present in three different forms: the dilactone (I) is present as the open D-ring form (monolactone), the limonoate A-ring lactone (II) and the glucoside form (III). Only the monolactones and glucosides are present in fruit tissues.

Compound III is the predominant limonoid glucoside found in all juice samples. In orange juice it comprises 56% of the total limonoid glucosides present, while in grapefruit and lemon juices, it comprises an average of 63% to 66% respectively. Procedures for the extraction and isolation of both aglycones and glucosides have been established to obtain concentrated sources of various limonoids.

Tocotrienols are present in palm oil and are a form of vitamin E having an unsaturated side chain. They include, but are not limited to alpha-tocotrienol, gamma-tocotrienol or delta-tocotrienol.

Soy Protein

Soy protein is a complete protein derived from soy beans. Soybean isoflavones for example, genistein, which is a minor component of soy protein preparations may have cholesterol-lowering effects. Recent studies suggest that soy protein and soy isoflavones, genistein and daidzein, might also be beneficial in insulin resistance and Type II diabetes.

Citrus limonoids, citrus flavonoids, tocotrienols or soy proteins may be formulated into pharmaceutical preparations for administration to mammals for prevention and treatment of insulin resistance, cardiovascular disease, hypercholesterolemia or atherosclerosis.

Many of the citrus limonoids, flavonoids, tocotrienols or soy proteins may be provided as compounds with pharmaceutically compatible counterions, a form in which they may be soluble.

Formulations containing the citrus limonoids, citrus flavonoids, tocotrienols and/or soy proteins of the present invention may be administered by any acceptable means including orally, transdermally, rectally, intravenously, intramuscularly, intraperitoneally, subcutaneously, topically, by inhalation or any other means. The oral administration means is preferred. Formulations suitable for oral administration are commonly known and include liquid solutions of the active compounds dissolved in a diluent such as, for example, saline, water, PEG 400, etc. Solid forms of the compounds for oral administration include capsules or tablets, each comprising the active ingredients and commonly known adjuvants. The active ingredients in the solid dosage form may be present in the form of solids, granules, gelatins, suspensions, and/or emulsions, as will be apparent to persons skilled in the art. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Formulations suitable for parenteral administration include aqueous and non aqueous isotonic sterile solutions containing buffers, antioxidants, preservatives and any other known adjuvants.

Useful solutions for oral or parenteral administration can be prepared by any of the methods well known in the pharmaceutical art, described, for example, in Remington's Pharmaceutical Sciences, 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets may be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible birding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Patient dosages for oral administration of citrus limonoids range from 1-500 mg/day, commonly 1-100 mg/day, and typically from 1-100 mg/day. Stated in terms of patient body weight, usual dosages range from 0.01-10 mg/kg/day, commonly from 0.01-2.0 mg/kg/day, typically from 0.01 to 2.0 mg/kg/day.

Patient dosages for oral administration of citrus flavonoids range from 200-5000 mg/day, commonly 1000-2000 mg/day, and typically from 500-1500 mg/day. Stated in terms of patient body weight, usual dosages range from 15-70 mg/kg/day, commonly from 15-30 mg/kg/day, typically from 7-21 mg/kg/day.

Patient dosages for oral administration of tocotrienols range from 1-1200 mg/day, commonly 1-100 mg/day, and typically from 1-60 mg/day. Stated in terms of patient body weight, usual dosages range from 0.01-20 mg/kg/day, commonly from 0.01-2.0 mg/kg/day, typically from 0.01 to 1/0 mg/kg/day.

Patient dosages for oral administration of soy protein range from 1-500 g/day, commonly 25-250 g/day, and typically from 25-100 g/day.

In certain preferred embodiments, the composition comprises about 300 mg polymethoxyflavones, about 100 mg hesperidin, about 100 mg naringin, about 30 mg limonoids and about 10 mg tocotrienols.

The above disclosure generally describes the present invention. A more complete understanding can be obtained by reference to the following specific examples which are provided herein for purposes of illustration only, and are not intended to limit the scope of the invention.

The following examples illustrate the use of the invention for glycemic control. They are intended to further illustrate the invention and are not intended to limit the scope of the invention as defined by the claims.

EXAMPLE

Subjects

Forty-nine subjects aged 18-75 years with fasting blood glucose levels between 5.2-15.4 mmol/L (95 to 280 mg/dl), HbA1c level of ≤12% and BMI of 25 to 40 kg/m2 were recruited through local advertisement and the clinic's electronic patient database. Subjects were permitted to be on prescribed medications for the control of diabetes and cardiovascular disease. Subjects were excluded for the following reasons: pregnant or breastfeeding, on medications affecting weight, use of insulin, history of heart disease, cancer, alcohol or drug abuse, participation in a clinical research trial within 30 days prior to randomization, had food restrictions, allergies or intolerances to the investigational product. All study investigations were conducted in accordance with the Declaration of Helsinki and in compliance with ICH Guidelines for Good Clinical Practices. This study was reviewed and approved by Integrative Ethical Review Board (Austin, Tex.). All subjects provided written informed consent prior to any study procedures.

Study Protocol

The study was a randomized, double blind, placebo-controlled, parallel study conducted at SIBR Research, Inc., West Bradenton, Fla., USA over a 24 week period, between June 2007 and October 2008.

At screening, inclusion and exclusion criteria, medical history and concomitant medications were reviewed. Heart rate, blood pressure, height, weight, hip and waist circumference were measured and BMI calculated. Fasting blood was collected for the determination of complete blood count, electrolytes (Na, K, Cl), kidney function (creatinine, creatinine kinase, protein), liver function (aspartate aminotransferase, alanine transaminase and bilirubin), glucose, HbA1c, and lipid profile (total cholesterol, HDL-C, LDL-C and triglycerides). Further, female subjects provided a urine sample for pregnancy testing.

At baseline and at all other visits blood pressure and heart rate were assessed, anthropometric measurements recorded, and BMI calculated. Fasting blood was collected for the determination of glucose, insulin and HbA1c. An oral glucose tolerance test (OGTT), where subjects consumed a 100 g glucose beverage over a 10 minute period, was conducted on all subjects at baseline and after 12 and 24 weeks. Briefly, blood samples collected at 30, 60, 120, 180 and 240 minutes post-glucose consumption were analyzed for glucose and insulin. Fasting blood was also collected at weeks 12 and 24 for the determination of complete blood count, electrolytes (Na, K, Cl), kidney function (creatinine, creatinine kinase, protein), liver function (aspartate aminotransferase, alanine transaminase and bilirubin), glucose, HbA1c, and lipid profile (total cholesterol, HDL-C, LDL-C and triglycerides). All assessments in blood were analyzed by a certified local laboratory.

Subjects maintained a diary for the duration of the study period to record concomitant therapies and adverse events. The subject diary was reviewed at each study visit.

Randomization and Blinding

Fifty subjects were eligible to participate in the study. Subjects were randomized in a 1:1 ratio to receive either a composition of an embodiment of the present invention or a placebo in five blocks of ten. Both products were encapsulated by Innovative Health Products, Largo, Fla. The test products were similar in shape, size, weight and color.

Product

The composition of an embodiment of the present invention (a citrus bioflavonoid complex formulation, 525 mg/capsule) and placebo (microcrystalline cellulose, 525 mg/capsule) were encapsulated by Innovative Health Products, Largo, Fla.

| Component | Amount |
| --- | --- |
| Assay (Polymethoxylated flavones By HPLC) | 71.84% |
| Nobiletin | 58.28% |
| Tangeretin | 13.56% |
| Synephrin | 0.35% |

In general, amounts of components may include: assay (polymethoxylated flavones by HPLC) greater than or equal to approximately 62%, nobiletin greater than or equal to 49%, tangeretin greater than or equal to approximately 13%, and synephrin less than or equal to approximately 0.5%.

Subjects were instructed to take two capsules per day, one capsule in the morning and one in the evening, with food for 24 weeks. Unused products were returned at each study visit to calculate treatment compliance.

Statistical Analysis

The intention-to-treat analysis included all subjects who were randomized into the study and who completed at least one post-baseline study visit. The completer's analysis included all subjects who completed all visits of the 6 month study.

Data is presented as means with standard deviations for those subjects completing the 24 week study; group descriptive statistics were calculated for each study group, and statistical comparisons of glucose and HbA1c were performed using Analysis of Covariance (ANCOVA) adjusting for baseline values. Statistical comparisons for baseline characteristics, lipid profiles, insulin response and measures of safety (hematology, blood chemistry, biometrics and vital signs) were performed using Analysis of Variance (ANOVA). Comparisons of area under the glucose and insulin concentration curves and maximum concentration (Cmax) were made using data that was log transformed prior to statistical comparisons, which is the preferred method for determination of area under the concentration curve. Within group comparisons of fasting glucose and 2 hour postprandial glucose were made using a t-test. Analysis of safety was based on all subjects randomized to either treatment and known to have taken at least one dose of test product. Subjects that did not meet the recommended goals for diabetes treatment (i.e. the reduction of vascular disease risk factors and diabetes control) were also reassessed after the 6 months of supplementation with the composition of an embodiment of the present invention or placebo, and the number of subjects that had achieved the recommended goals were identified and categorized accordingly.

Results

There were no differences in baseline characteristics of the 49 subjects randomized to treatment (Table 1). Thirty four subjects completed the trial, and subject characteristics were similar between groups (Table 2). There were 16 withdrawals during the study, however the number of withdrawals was not significant between groups (P=0.36).

14.3% of subjects achieved the recommended goal for HbA1c (≤7%) after 12 weeks of supplementation in the composition of an embodiment of the present invention group compared to 0% in the placebo group. 33.3% of the subjects on the composition of an embodiment of the present invention achieved an LDL-C≤100 mg/dL while only 15.4% achieved the same goal when on placebo. 20.0% of subjects on the composition of an embodiment of the present invention achieved total cholesterol levels ≤200 mg/dL compared to 12.5% in placebo. 83.3% of subjects on the composition of an embodiment of the present invention achieved systolic blood pressure ≤130 mmHg as compared to 60% of subjects on placebo (Table 3).

Glucose tolerance tests at baseline, week 12 and week 24 demonstrated a peak in blood glucose at 120 minutes, with levels at 240 minutes remaining above fasting levels (0 minutes) (FIGS. 1a and 1b). Both groups showed a mean increase in AUC (0-240 minutes) and Cmax from baseline to weeks 12 and 24. There was no between group statistical significance in the maximum concentration (Cmax) of glucose or AUC(0-240 minutes) at baseline, week 12 or week 24. The time to maximum concentration (Tmax) of serum glucose was significantly longer for subjects on the composition of an embodiment of the present invention as compared to placebo at week 12 (P=0.01). This difference was not sustained through week 24. Fasting glucose and 2-hour postprandial glucose levels increased from baseline to week 24 in subjects of both groups, but to a lesser extent in subjects on the composition of an embodiment of the present invention. The within group increase in fasting glucose of subjects on placebo showed a trend toward significance at week 12 (P=0.08) and reached statistical significance at week 24 (P=0.05). Although the composition of an embodiment of the present invention group showed an increase from baseline to week 12 and week 24, the increases were not statistically significant (P=0.85 and P=0.67, respectively). A significant within group increase in 2 hour postprandial glucose levels was seen in the placebo group from baseline to week 12 (P=0.05) and continued to trend toward significance at week 24 (P=0.07). The within group change in 2 hour post-prandial glucose from baseline to week 12 and baseline to week 24 was not statistically significant for subjects on the composition of an embodiment of the present invention (Table 4).

In subjects completing the study that had all three of the following criteria: fasting glucose >100 mg/dL, 2 hour post-prandial glucose >140 mg/dL and HbA1c of >7%; the fasting blood glucose and OGTT profiles at week 12 and 24 were higher than those at baseline for subjects on placebo. In the composition of an embodiment of the present invention group, OGTT excursions at week 12 and 24 remained similar to the baseline profile (FIGS. 1c and 1d). Subjects on the composition of an embodiment of the present invention demonstrated higher fasting insulin levels at all time points from baseline to week 24 in comparison to placebo (Table 4). After 24 weeks of supplementation, the four hour insulin curve showed a blunting of the curve, which was not seen in subjects on placebo (FIGS. 2a and 2b).

Serum HbA1c levels did not differ significantly between the composition of an embodiment of the present invention and placebo groups. The lipid panel (total cholesterol, triglycerides, LDL-C and HDL-C) improved for subjects in the composition of an embodiment of the present invention group when compared with the placebo group, with a decreased trend in total cholesterol and LDL-C, and an increasing trend in HDL-C levels observed from baseline to week 24. Subjects on placebo demonstrated increases in total cholesterol, triglycerides and LDL-C and a decrease in HDL-C from baseline to week 24, however, the differences between groups were not significant (Table 5).

Biometric measures (weight, BMI, waist circumference, hip circumference and waist-to-hip ratio) were consistent across both groups from baseline to week 24. Vital signs (systolic blood pressure, diastolic blood pressure and heart rate) were not significantly different between the composition of an embodiment of the present invention group and placebo group after 24 weeks of supplementation.

Safety

There were no significant differences between groups with respect to any hematology or clinical measures of safety including CBC, electrolytes, kidney and liver function markers, at any point during the study. A total of four adverse events were assessed by the investigator as having a possible or probable relationship to treatment, 3 in the composition of an embodiment of the present invention group (diarrhea, N=2; indigestion, N=1) and 1 in the placebo group (nausea, N=1). These assessments were made while the study was still blinded. Test article was discontinued for the two subjects reporting diarrhea.

TABLE 1

Baseline characteristics of subjects in the intention-to-treat analysis

|  | Composition (N = 22) [N] Mean (SD) | Placebo (N = 21) [N] Mean (SD) | P Value♦ |
|---|---|---|---|
| Age (years) | [22] 57.8 (11.5) | [21] 57.2 (8.1) | 0.85 |
| Gender {f/n (%)} |  |  |  |
| Male | 12/22 (54.5%) | 12/21 (57.1%) | 1.00† |
| Female | 11/22 (45.5%) | 9/21 (42.9%) |  |
| On Diabetic Medication {f/n (%)} | 16/22 (72.7%) | 16/21 (76.2%) | 1.00† |
| Height (m) | [22] 1.7 (0.1) | [21] 1.7 (0.1) | 0.83 |
| Weight (kg) | [22] 101.6 (30.9) | [21] 104.3 (20.7) | 0.74 |
| BMI (kg/m2) | [22] 34.8 (7.3) | [21] 35.8 (5.3) | 0.60 |
| Waist Circumference (cm) | [22] 111.2 (18.5) | [21] 113.7 (13.2) | 0.61 |
| Hip Circumference (cm) | [22] 117.8 (16.1) | [21] 120.9 (15.0) | 0.52 |
| Waist to Hip Ratio | [22] 0.95 (0.09) | [21] 0.94 (0.08) | 0.70 |

♦Statistical comparisons were performed using Analysis of Variance (ANOVA).
†Statistical comparisons were performed using Fisher's Exact Test.

TABLE 2

Baseline characteristics of subjects on the composition of an embodiment of the present invention or placebo for 6 months completing the study

|  | Composition (N = 15) [N] Mean (SD) | Placebo (N = 19) [N] Mean (SD) | P Value♦ |
|---|---|---|---|
| Age (years) | [15] 58.5 (13.0) | [19] 57.7 (7.7) | 0.84 |
| Gender {f/n (%)} |  |  |  |
| Male | 7/15 (46.7%) | 10/19 (52.6%) | 1.00† |
| Female | 8/15 (53.3%) |  |  |
| On Diabetic Medication {f/n (%)} | 12/15 (80.0%) | 14/19 (73.7%) | 1.00† |
| Height (m) | [15] 1.7 (0.1) | [19] 1.7 (0.1) | 0.98 |
| Weight (kg) | [15] 99.3 (30.6) | [19] 99.7 (12.0) | 0.96 |
| BMI (kg/m2) | [15] 34.5 (7.8) | [19] 35.1 (4.4) | 0.77 |
| Waist Circumference (cm) | [15] 109.2 (16.7) | [19] 111.0 (9.7) | 0.52 |
| Hip Circumference (cm) | [15] 117.5 (16.0) | [19] 118.1 (10.3) | 0.83 |
| Waist to Hip Ratio | [15] 0.93 (0.09) | [19] 0.94 (0.08) | 0.73 |

♦Statistical comparisons were performed using Analysis of Variance (ANOVA).
†Statistical comparisons were performed using Fisher's Exact Test.

TABLE 3

Subjects that did not meet the recommended goals for diabetes treatment were identified at baseline. These subjects were assessed after 6 months of supplementation with the composition of an embodiment of the present invention or placebo. The number of subjects that achieved goals for vascular disease risk factors and diabetes control were identified after 6 months of supplementation with the composition of an embodiment of the present invention and were categorized accordingly.

|  | Composition (n = 15) | Placebo (n = 19) |
|---|---|---|
|  | Subjects Above Goals at Baseline {f/n (%)} | Subjects Above Goals at Baseline {f/n (%)} |
| OGTT 2 h ≤140 mg/dL | 15/15 (100.0%) | 18/19 (94.7%) |
| LDL-c ≤100 mg/dL | 9/15 (60.0%) | 13/19 (68.4%) |
| HbA1c ≤7% | 7/15 (46.7%) | 4/19 (21.1%) |
| Total Cholesterol ≤200 mg/dL | 5/15 (33.3%) | 8/19 (42.1%) |
| Systolic BP ≤130 mmHg | 6/15 (40.0%) | 10/19 (52.6%) |
|  | Subjects above goals at baseline who achieve goals at week 24 {f/n (%)} | Subjects above goals at baseline who achieve goals at week 24 {f/n (%)} |
| OGTT 2 h ≤140 mg/dL | 1/15 (6.7%) | 0/18 (0.0%) |
| LDL-c ≤100 mg/dL | 3/9 (33.3%) | 2/13 (15.4%) |
| HbA1c ≤7% | 1/7 (14.3%) | 0/4 (0.0%) |
| Total Cholesterol ≤200 mg/dL | 1/5 (20.0%) | 1/8 (12.5%) |
| Systolic BP ≤130 mmHg | 5/6 (83.3%) | 6/10 (60.0%) |

TABLE 4

Fasting blood glucose levels and 2-hour post-prandial glucose at baseline and week 12 and 24 for subjects who were completers on the composition of an embodiment of the present invention or placebo

|  | Study group | | |
|---|---|---|---|
|  | Composition (n = 15) [N] Mean ± SD | Placebo (n = 19) [N] Mean ± SD | P value$^\phi$ |
| Fasting Glucose (mg/dL) | | | |
| Baseline(Week 0) | [15] 151.5 ± 18.3 | [19] 143.0 ± 46.2 | — |
| Week 12 | [15] 153.3 ± 36.8 | [19] 167.4 ± 69.5 | 0.23 |
| Week 24 | [15] 158.5 ± 54.0 | [19] 165.5 ± 68.9 | 0.46 |
| Change from baseline to Week 12 | [15] 1.8 ± 36.9 P = 0.85 | [19] 24.4 ± 57.5 P = 0.08 | 0.20 |
| Change from baseline to Week 24 | [15] 7.0 ± 62.2 P = 0.67 | [19] 22.5 ± 47.8 P = 0.05 | 0.42 |
| 2 Hour Glucose (mg/dL) | | | |
| Baseline(Week 0) | [15] 311.3 ± 69.8 | [19] 296.9 ± 94.1 | — |
| Week 12 | [15] 330.3 ± 86.2 | [19] 329.7 ± 101.5 | 0.54 |
| Week 24 | [15] 328.8 ± 101.7 | [19] 326.2 ± 103.7 | 0.63 |
| Change from baseline to Week 12 | [15] 19.1 ± 37.6 P = 0.07 | [19] 32.7 ± 69.0 P = 0.05 | 0.50 |
| Change from baseline to Week 24 | [15] 17.5 ± 63.1 P = 0.30 | [19] 29.3 ± 66.2 P = 0.07 | 0.60 |
| Fasting Insulin (uIU/mL) | | | |
| Baseline | [15] 14.5 (10.8) | [19] 16.1 (18.0) | 0.91 |
| Week 12 | [15] 19.1 (17.8) | [19] 14.5 (12.9) | 0.39 |
| Week 24 | [15] 16.7 (15.7) | [19] 14.3 (14.5) | 0.65 |

$^\phi$Between group statistical comparisons were performed using Analysis of Covariance (ANCOVA) adjusting for baseline values.
Within group statistical comparisons were performed using a t-test.

TABLE 5

Serum lipid profile of subjects supplemented with the composition of an embodiment of the present invention or placebo at baseline, week 12 and week 24 during the 6 month study.

|  | The composition of an embodiment of the present invention (N = 15) [N] Mean (SD) | Placebo (N = 19) [N] Mean (SD) | P-Value |
|---|---|---|---|
| Total Cholesterol (mg/dL) | | | |
| Baseline | [15] 182.7 (42.3) | [19] 182.6 (50.0) | 0.99 |
| Week 12 | [15] 179.9 (39.0) | [19] 189.3 (44.0) | 0.52 |
| Week 24 | [15] 179.6 (36.4) | [19] 202.4 (59.0) | 0.20 |
| Triglycerides (mg/dL) | | | |
| Baseline | [15] 180.9 (125.0) | [19] 166.9 (88.1) | 0.70 |
| Week 12 | [15] 186.0 (104.4) | [19] 201.5 (118.0) | 0.69 |
| Week 24 | [15] 209.9 (130.3) | [19] 294.0 (315.5) | 0.34 |
| LDL-c (mg/dL) | | | |
| Baseline | [15] 111.7 (28.1) | [19] 114.1 (37.4) | 0.84 |
| Week 12 | [15] 111.6 (31.2) | [19] 116.5 (37.3) | 0.69 |
| Week 24 | [15] 105.2 (29.4) | [19] 120.2 (41.8) | 0.25 |
| HDL-c (mg/dL) | | | |
| Baseline | [15] 38.7 (9.6) | [19] 40.8 (13.0) | 0.60 |
| Week 12 | [15] 38.6 (9.5) | [19] 40.3 (11.9) | 0.65 |
| Week 24 | [15] 39.3 (12.0) | [19] 38.8 (11.2) | 0.90 |

$^\phi$Statistical comparisons were performed using Analysis of Variance (ANOVA).

Fasting blood glucose levels for subjects on placebo showed a 17% and 16% (P=0.05) increase from baseline to week 12 and week 14, respectively. However those on the composition of an embodiment of the present invention showed only a 1.2% and 5% increase from baseline at week 12 and week 24. Two hour post-prandial glucose levels followed a similar trend with subjects on placebo showing an 11% (P=0.05) and 10% (P=0.07) increase from baseline at week 12 and week 24 respectively with those on the composition of an embodiment of the present invention showing smaller increases of 6% at both week 12 and 24. A progressive shift occurs in the contribution of fasting and post-prandial hyperglycemia when patients progress from mild to moderate hyperglycemia. These results are in agreement with those reported in the literature where fasting blood glucose is known to increase as diabetes progresses and worsens. The significant within group increase in fasting glucose and 2 h post prandial glucose in the placebo group despite being on medication confirms that conventional therapies alone are inadequate in control of the progression of disease and that the composition of an embodiment of the present invention when added to the treatment model worked to decrease the elevation of these important surrogate biomarkers.

Analysis of diurnal glycemic profiles of non-insulin treated diabetics found that post prandial hyperglycemia excursions are a strong predictor of cardiovascular disease compared to fasting glucose. Completers in both groups showed similar excursion in the OGTT curve from baseline to week 12 and 24 however those on the composition of an embodiment of the present invention showed excursions that stayed close to their baseline profiles at week 12 and 24. This was reflected by the significantly longer Tmax than those on placebo at week 12. Higher fasting insulin at all time points from baseline to week 24 in subjects on the composition of an embodiment of the present invention supported the smaller increases in fasting glucose in this group of subjects compared to those in placebo. When comparing the FG and OGTT excursions of subjects that were not meeting all three diabetic targets at baseline (FG>100 mg/dL, 2 hour postprandial glucose >140 mg/dL and HbA1c of >7%) the OGTT excursions at week 12 and 24 for subjects on placebo were higher supporting the significantly higher FG and 2 h PP glucose in this group. Subjects in the composition of an embodiment of the present invention group showed OGTT excursions at week 12 and 24 that remained similar to the excursions that were seen at baseline and are supported by the significantly longer Tmax, smaller increase in FG and 2 h PP and higher levels of fasting insulin. It is apparent that conventional treatments alone are inadequate to control post-prandial glycemia and the resulting fluctuations in blood glucose. Furthermore, glycemic control rates are lowest for diabetic subjects also diagnosed with hypertension, hyperlipidemia and/or obesity.

The completers analysis showed that subjects on the composition of an embodiment of the present invention had decreasing trends in total cholesterol (1.5%), LDL-C(5.8%) and increasing trends in HDL-C(1.6%) while subjects on placebo showed an increase in total cholesterol (11%), LDL-C(5.3%) and a decrease in HDL-C(4.9%). The natural progression of the disease was evident in subjects on placebo in spite of receiving appropriate drug therapy for diabetes and associated co-morbidities.

Most available glycemic control treatments have been used in combination to lower blood glucose in type 2 diabetes. A rational selection for combined diabetes therapy would include therapies which lower glucose production, increase insulin levels and control cardiovascular risk. The current study suggests a role for the composition of an embodiment of the present invention in the management of type 2 diabetes and for decreasing surrogate risk biomarkers providing cardio protection in subjects in a wide age range on conventional therapy. It was also demonstrated that the composition of an embodiment of the present invention worked synergistically with the subjects' medication to improve and achieve diabetic treatment goals.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A method comprising administering an effective amount of a composition to a subject diagnosed with diabetes, wherein the subject is currently taking one or more prescribed medications for control of diabetes, wherein the one or more prescribed medications are selected from the group consisting of: metformin, acarbose, fibrates, thiazolidienodiones, Sulphonylureas, and combinations thereof, wherein the subject does not have the following: HbA1c≤7%; LDL-C≤100 mg/dL; total cholesterol≤200 mg/dL; and systolic blood pressure≤130 mmHg, wherein after a predetermined period of supplementation with the composition, the subject has at least one of the following: HbA1c≤7%; LDL-C≤100 mg/dL; total cholesterol≤200 mg/dL; and systolic blood pressure≤130 mmHg; and
    wherein the composition comprises at least one polymethoxyflavone.

2. The method of claim 1, wherein the one or more prescribed medications are metformin.

3. The method of claim 1, wherein the composition comprises about 300 mg of the at least one polymethoxyflavone.

4. The method of claim 1, wherein the composition comprises greater than or equal to approximately 62% of the at least one polymethoxyflavone.

5. The method of claim 1, wherein the composition further comprises at least one limonoid, at least one flavonoid and at least one tocotrienol.

6. The method of claim 5, wherein the composition comprises 1-500 mg/day of the at least one liminoid.

7. The method of claim 6, wherein the composition comprises 1-100 mg/day of the at least one liminoid.

8. The method of claim 5, wherein the composition comprises 200-5,000 mg/day of the at least one flavinoid.

9. The method of claim 8, wherein the composition comprises 500-1,500 mg/day of the at least one flavinoid.

10. The method of claim 5, wherein the composition comprises 1-1,200 mg/day of the at least one tocotrienol.

11. The method of claim 10, wherein the composition comprises 1-60 mg/day of the at least one tocotrienol.

12. The method of claim 1, wherein the composition further comprises soy protein.

13. The method of claim 12, wherein the composition comprises 1-500 mg/day of the soy protein.

14. The method of claim 13, wherein the composition comprises 25-100 mg/day of the soy protein.

15. The method of claim 5, wherein the composition comprises about 300 mg of the at least one polymethoxyflavone, and further comprises about 30 mg of at least one liminoid, about 200 mg of at least one flavinoid, and about 10 mg of at least one tocotrienol.

16. The method of claim 1, wherein the subject is a human.

17. The method of claim 1, wherein the predetermined period of supplementation is at least 12 weeks.

18. The method of claim 17, wherein the predetermined period of supplementation is at least 24 weeks.

19. The method of claim 1, wherein the composition is administered orally, transdermally, rectally, intravenously, intramuscularly, intraperitoneally, subcutaneously, topically, or by inhalation.

* * * * *